United States Patent [19]

Zaromb

[11] Patent Number: 5,322,611
[45] Date of Patent: Jun. 21, 1994

[54] HUMIDITY-RESISTANT AMBIENT-TEMPERATURE SOLID-ELECTROLYTE AMPEROMETRIC SENSING APPARATUS

[76] Inventor: Solomon Zaromb, 9S 706 William Dr., Hinsdale, Ill. 60521

[21] Appl. No.: 648,649

[22] Filed: Jan. 31, 1991

[51] Int. Cl.$^5$ .................................... G01N 27/407
[52] U.S. Cl. .......................... 204/424; 204/153.14; 204/153.2; 204/421
[58] Field of Search ............... 204/153.18, 421–429, 204/419; 429/33

[56] References Cited

U.S. PATENT DOCUMENTS

| | | | |
|---|---|---|---|
| Re. 31,916 | 6/1985 | Oswin et al. | 204/432 |
| 3,719,564 | 3/1973 | Lilly et al. | 204/153.18 |
| 3,764,269 | 10/1973 | Oldham et al. | |
| 3,821,090 | 6/1974 | Topol et al. | 204/426 |
| 4,040,929 | 8/1977 | Bauer et al. | 204/426 |
| 4,083,764 | 4/1978 | van de Leest et al. | 204/419 |
| 4,591,414 | 5/1986 | Zaromb et al. | 204/415 |
| 4,824,528 | 4/1989 | Polak et al. | 204/153.18 |
| 4,851,303 | 7/1989 | Madou et al. | 429/33 |
| 5,128,020 | 7/1992 | Yamaguchi et al. | 204/421 |

Primary Examiner—T. Tung

[57] ABSTRACT

Apparatus and methods for detecting selected chemical compounds in air or other gas streams at room or ambient temperature includes a liquid-free humidity-resistant amperometric sensor comprising a sensing electrode and a counter and reference electrode separated by a solid electrolyte. The sensing electrode preferably contains a noble metal, such as Pt black. The electrolyte is water-free, non-hygroscopic, and substantially water-insoluble, and has a room temperature ionic conductivity $\geq 10^{-4}$ (ohm-cm)$^{-1}$, and preferably $\geq 0.01$ (ohm-cm)$^{-1}$. The conductivity may be due predominantly to Ag+ ions, as in $Ag_2WO_4 \cdot 4AgI$, or to F− ions, as in $Ce_{0.95}Ca_{0.05}F_{2.95}$. Electrical contacts serve to connect the electrodes to potentiostating and detecting circuitry which controls the potential of the sensing electrode relative to the reference electrode, detects the signal generated by the sensor, and indicates the detected signal.

6 Claims, 2 Drawing Sheets

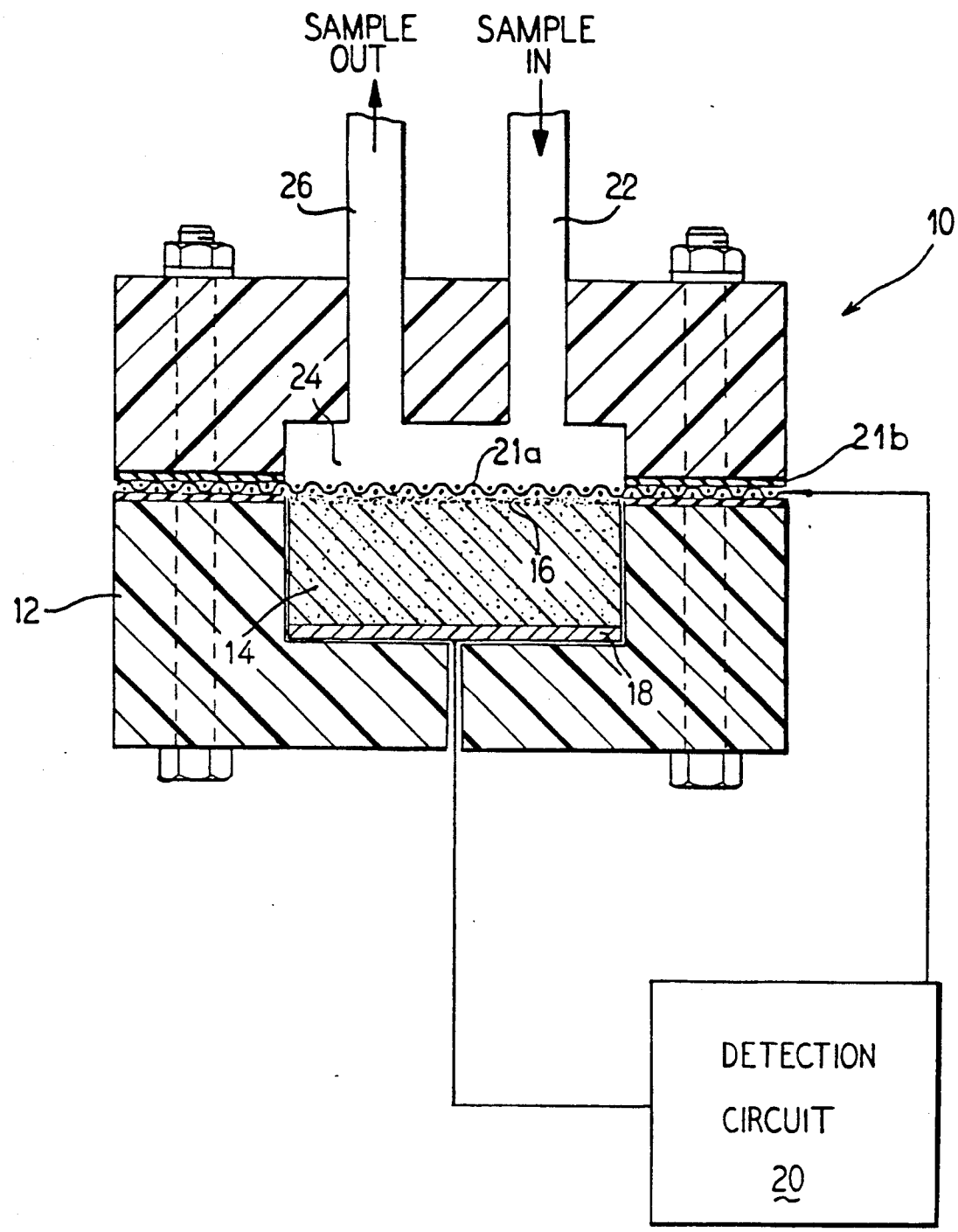

HUMIDITY-RESISTANT AMBIENT-TEMPERATURE SOLID-ELECTROLYTE AMPEROMETRIC SENSING APPARATUS

CONTRACTUAL ORIGIN OF INVENTION

The U.S. Government has rights in this invention pursuant to Contract No. W-31-109-ENG-38 between the U.S. Department of Energy and the University of Chicago representing Argonne National Laboratory. The U.S. Department of the Interior, Bureau of Mines, funded the work that lead to the invention.

BACKGROUND OF THE INVENTION

This invention relates to chemical sensing apparatus and methods, and more particularly to apparatus comprising a solid-electrolyte, solvent-free, moisture-resistant amperometric sensor. Certain air contaminants may be either directly hazardous—e.g., acutely toxic or carcinogenic compounds, such as carbon monoxide (CO), formaldehyde ($H_2CO$), hydrazine ($N_2H_4$), methyl hydrazine ($CH_3N_2H_3$) or dimethyl hydrazine [$(CH_3)_2N_2H_2$]—or they may be indicative of a hazard—e.g., methane ($CH_4$) in coal mines or ethanol ($CH_3CH_2OH$) in the driver's seat of a moving motor vehicle. Early detection of such compounds may permit or trigger timely actions (e.g., disabling an automobile ignition system) to prevent death or injury.

Although various detectors for such compounds exist, they are usually bulky and expensive. Commercially available electrochemical sensors are relatively small and cheap, but they usually require an aqueous or non-aqueous liquid electrolyte solution which necessitates proper containment and periodic replenishments (following evaporation or other losses). To extend the time intervals between replenishments, a liquid reservoir is usually provided that is much larger than what is needed for the sensing function, which in turn enlarges the size and weight of the sensor. The sensors are exposed to the air that is to be monitored or analyzed and interact therewith so as to produce a detectable signal or change in the presence of selected compounds. The electrochemical detectors may be of either of two different types, namely potentiometric or amperometric. The potentiometric sensors are usually less accurate than amperometric sensors and have several other disadvantages.

Amperometric sensors, which exhibit current flow that is proportional to the concentration of an analyte, usually contain a liquid electrolyte, either aqueous or non-aqueous. The liquid electrolyte may sometimes be gelled or confined within a water-permeated ion-exchange polymer. Such sensors, as well as their operating mechanisms and associated detection or measuring circuitry, are well known in the art. Most heretofore disclosed solid-state, solvent-free amperometric sensors require elevated temperatures for operation.

Ambient-temperature amperometric sensors comprising the solid-state ionic conductor silver rubidium iodide ($Ag_4RbI_5$) have been disclosed in Japanese Patent No. 142266, issued in June 1987, for the detection of nitric oxide (NO), and by Buttner et al. (Proceedings of the 1987 Scientific Conference on Chemical Defense Research, 17–20 Nov. 1987, U.S. Army Chemical Research, Development, and Engineering Center, Aberdeen Proving Ground, Md., CRDEC-SP-88013, 1988, Vol. 2, pp. 1011-1017) for the detection of NO, CO, $N_2H_4$ and $CH_3N_2H_3$. However, the lifetime of the $Ag_4RbI_5$-based sensors turned out to be rather brief (<3 months) due to instability of $Ag_4RbI_5$ to moisture in the air.

Other reported solid-electrolyte sensors operate at elevated temperatures (>100° C.) and/or in the potentiometric mode. An amperometric sensor for the room temperature detection of methane is disclosed by Zaromb et al. in U.S. Pat. No. 4,591,414, issued on May 27, 1986. In this sensor, the potential of the sensing electrode is set high enough to effect the electro-oxidation of methane even at room temperature. However, the liquid non-aqueous electrolyte that is required to withstand the highly oxidizing working electrode potential presents confinement and replenishment problems.

It is therefore an object of this invention to provide an all-solid-state (i.e., substantially liquid-free) and room- or ambient-temperature-operating amperometric sensor for chemical detection that is not adversely affected by humidity.

It is another object of the invention to provide a chemical sensing apparatus comprising a long-lasting humidity-resistant solid-electrolyte amperometric sensor that operates at ambient temperature.

It is yet another object of the invention to provide a chemical sensing apparatus comprising an array of differently selective, miniaturized, solid-electrolyte sensors for the selective detection of various hazardous or hazard-indicative air contaminants.

It is still another object of the invention to provide apparatus for the detection of hazardous or hazard-indicative compounds such as CO, NO, $H_2CO$, $N_2H_4$, $CH_3N_2H_3$, $(CH_3)_2N_2H_2$, $CH_4$, or $CH_3CH_2OH$ comprising one or more miniaturized, solid-electrolyte ambient-temperature amperometric sensors.

These and other objects of this invention will become apparent from the following description and appended claims.

SUMMARY OF THE INVENTION

A chemical detector having a sensor of the amperometric type, that is solid-state, solvent-free, humidity-resistant and capable of operation at ambient or room temperature, is disclosed herein. The general characteristics of such a sensor are discussed hereinafter. The sensor comprises a solid electrolyte that is ionically conductive at room temperature and that is substantially free of hygroscopic or water-soluble components. There are many electrolytes satisfying the conductivity and water insolubility requirements. Two illustrative sensor electrolytes have the chemical composition $Ag_2WO_4 \cdot 4AgI$ or $Ce_{0.95}Ca_{0.05}F_{2.95}$. Amperometric sensors based on these electrolytes are not adversely affected by humidity and are sensitive to selected compounds exhibiting measurable responses upon exposure thereto. The solid-electrolyte is in intimate contact with two electrodes, at least one of which is preferably a noble metal catalyst. Such electrodes may comprise silver (Ag), platinum (Pt), gold (Au), and other noble metals. The electrodes are connected to known detection circuitry which measures current signals that are approximately proportional to the concentration of the analyte.

BRIEF DESCRIPTION OF THE DRAWING

The invention may be best explained with reference to the drawings, in which:

FIG. 1 schematically shows a detector including a housing, a sensor, and detection circuitry.

DESCRIPTION OF THE PREFERRED EMBODIMENTS

Figure 2A:
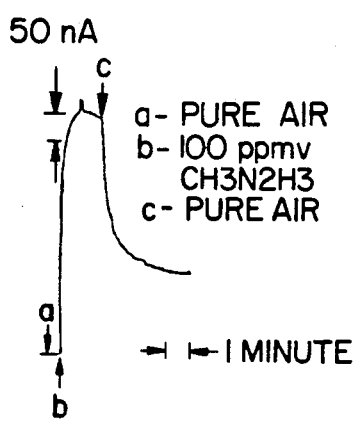
FIGS. 2A, 2B and 2C show illustrative response curves obtained with a preferred embodiment of the invention.

Referring to FIG. 1, there is shown a gas detector 10 comprising a housing 12 through which gas can flow. A solid-electrolyte 14 in contact with a sensing electrode 16 and a counter electrode 18 and detection circuitry 20 are also provided. A platinum (Pt) screen 21a, supported by the housing 12 and rubber pads, such as 21b, is pressed against the electrode 16 and connects the electrode 16 to the detection circuit 20. The sensor is the combination of the electrolyte 14 and electrodes 16 and 18. The gas flows through inlet 22 into a sample chamber 24 and exits through outlet 26. Electrodes 18, e.g., silver (Ag), and 16, usually a porous noble metal, such as platinum black, contact electrolyte 14 and are connected to detector circuitry 20. Part of the gas in chamber 24 reaches the interface between electrolyte 14 and sensing electrode 16, and gives rise to an electrochemical reaction which generates an electrical current that is measured by detection circuit 20. The detector circuitry, including an adjustable potentiostat, is well known in the art as, for example, disclosed in Bard & Faulkner, *Electrochemical Methods*, pp. 563, 556, Wiley.

The electrolyte in one preferred embodiment of the invention is a silver tungstate-silver iodide material having the chemical composition $Ag_2WO_4 \cdot 4AgI$. This material can be produced by mixing stoichiometric quantities of commercially available powdered $Ag_2WO_4$ and AgI, melting the mixture at a temperature of 500°-600° C., allowing the melt to cool, and grinding it to a powder with a mortar and pestle.

In one specific example, a 0.001-inch thick by 0.4-inch diameter silver disc was inserted in a 0.5-inch diameter die and covered with a 0.1-inch thick layer of powdered $Ag_2WO_4 \cdot 4AgI$. This was covered in turn with a thin layer of powdered silver (II) oxide ($Ag_2O_2$), and the assembly was compressed in the die at 16,000 psi for four minutes. The resulting pellet was covered on the silver oxide side with a thin layer of Pt black and compressed at slightly less than 300 psi for 30 seconds. The resulting sensor structure was inserted into the cavity of the housing 12 of FIG. 1 with the Pt black sensing electrode 16 contacting the platinum screen 21a. The housing 12 was covered with black tape so as to prevent light from reaching the light-sensitive component, AgI, of the sensor pellet. In order to detect different gases, the sensing electrode is electrically biased at different potentials. In order to differentiate between different compounds, arrays or a plurality of sensors at different biases can be used. For example, methylhydrazine or carbon monoxide can be detected with a Pt black sensing electrode biased at a potential of about 0.4 V relative to the silver counter electrode, whereas detection of methane requires a potential of about 0.8 V or higher. To protect the AgI component of the solid-electrolyte from oxidation at the potential of 0.8 V or higher, a thin buffer layer of $Ag_2O_2$ was interposed between the Pt black and the $Ag_2WO_4 \cdot 4AgI$.

Figure 2B:
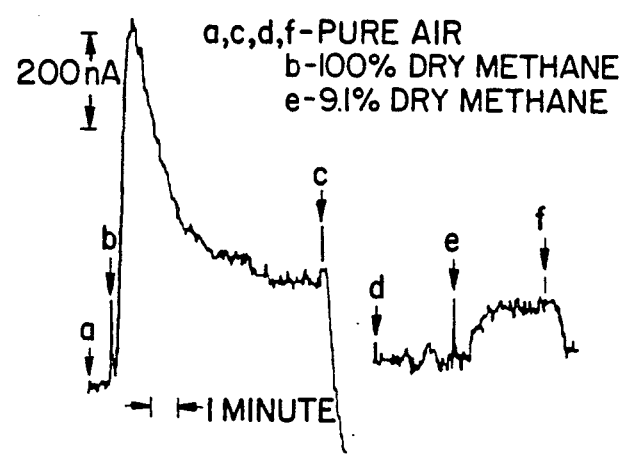
Figure 2C:
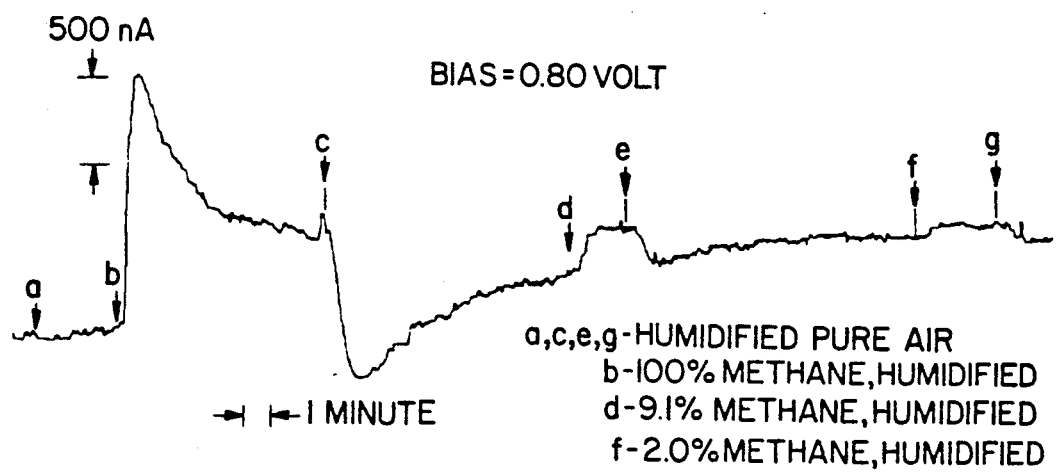

Then air containing methylhydrazine or methane was passed through the sensor. The compounds were present in various concentrations and produced the results shown in the following Table I. FIGS. 2A, 2B, and 2C illustrate some of the sensor responses that are listed in the table.

TABLE I

RESPONSES OF A SILVER TUNGSTATE-SILVER IODIDE ($Ag/Ag_2WO_4 \cdot 4AgI/Ag_2O_2/Pt$) SENSOR

| Sensing Electrode Potential* (V) | Gas Tested | Sensor Response (Microampers) |
|---|---|---|
| 0.40 | 100 ppmv≠ $CH_3N_2H_3$ | 0.31#,a |
| 0.80 | 100% $CH_4$ (dry) | 2.40# |
| 0.80 | 100% $CH_4$ (dry) | 0.86#,b |
| 0.80 | 9.1% $CH_4$ (dry) | 0.10#,b |
| 0.80 | 100% $CH_4$ (humidified) | 1.25#,c |
| 0.80 | 9.1% $CH_4$ (humidified) | 0.25#,c |
| 0.80 | 2% $CH_4$ (humidified) | 0.063#,c |
| 0.90 | 100% $CH_4$ (dry) | 0.35** |
| 0.90 | 100% $CH_4$ (humidified) | 0.25** |

*Potential relative to the silver counter and reference electrode 18
≠ppmv = parts per million by volume
Measured on the third day following sensor construction
**Measured 8 months following sensor construction
a See FIG. 2a
b See FIG. 2b
c See FIG. 2c In a second preferred embodiment of the invention, the electrolyte has the chemical composition $Ce_{0.95}Ca_{0.05}F_{2.95}$. This material can be produced by a) mixing solutions of cerous nitrate and calcium chloride, in a stoichiometric ratio, with an excess of hydrofluoric acid, and b) filtering, washing, and drying the resulting precipitate. The dried precipitate can be ground to a fine powder in a mortar and pestle prior to introduction in a pelletizing die.

In one specific example, a 0.001-inch thick by 0.4-inch diameter disc of tin foil was introduced into a 0.5-inch diameter pelletizing die and covered with a 0.1-inch thick layer of finely powdered $Ce_{0.95}Ca_{0.05}F_{2.95}$. After compressing the powder at 16,000 psi for four minutes, a thin layer of Pt black was added and pressed into the pellet at slightly less than 300 psi for 30 seconds. The resulting sensor pellet was inserted in the cavity of the housing 12 of FIG. 1, with the Pt black sensing electrode 16 contacting the platinum screen 21a and the tin foil counter electrode contacting a silver disc 18.

Then air containing carbon dioxide, water vapor or methane was passed through the sensor and produced the responses listed in the following Table II.

TABLE II

RESPONSES OF A CERIUM CALCIUM FLUORIDE ($Sn/Ce_{0.95}Ca_{0.05}F_{2.95}/Pt$) SENSOR

| Sensing Electrode Potential* (V) | Gas Tested | Sensor Response (Microampers) |
|---|---|---|
| 0.40 | 200 ppmv CO | 1.75# |
| 0.40 | Dry air | 0# |
| 0.40 | Humidified air, 10% RH≠ | 0# |
| 0.40 | Humidified air, 50% RH≠ | 0# |
| 0.40 | Humidified air, 100% RH≠ | 0# |
| 0.80 | 100% $CH_4$ (dry) | 0.049** |
| 0.80 | 9.1% $CH_4$ (dry) | 0.025** |
| 0.80 | 100% $CH_4$ (humidified) | 0.049** |
| 1.75 | 100% $CH_4$ (dry) | 0.017≠≠ |
| 1.75 | 9.1% $CH_4$ (dry) | 0.001≠≠ |

*Potential relative to the tin counter and reference electrode
≠RH = relative humidity
Measured one day after sensor construction
**Measured two days after sensor construction
≠≠Measured six days after sensor construction In another specific example, a cerium calcium fluoride sensor prepared in the same manner as in the immediately preceding example, elicited the responses listed in the following Table III.

TABLE III
RESPONSES OF A SECOND CERIUM CALCIUM FLUORIDE (Sn/Ce$_{0.95}$Ca$_{0.05}$F$_{2.95}$/Pt) SENSOR

| Sensing Electrode Potential* (V) | Gas Tested | Sensor Response (Microampers) |
|---|---|---|
| 0.40 | 100 ppmv CH$_3$N$_2$H$_3$ | 0.90≠ |
| 1.0 | 100% CH$_4$ (dry) | 0.21≠ |
| 1.0 | 9.1% CH$_4$ (dry) | 0.013≠ |
| 1.0 | 100% CH$_4$ (humidified) | 0.12≠ |
| 1.0 | 9.1% CH$_4$ (humidified) | 0.006≠ |
| 0.90 | 100% CH$_4$ (dry) | 0.015# |
| 0.90 | 9.1% CH$_4$ (dry) | 0.004# |

*Potential relative to the tin counter and reference electrode
≠Measured one day after sensor construction
Measured eight months after sensor construction The occasional deviations from proportionality between the measured methane concentrations and the response currents may be due to a saturation effect at concentrations above about 10% methane.

Thus it is seen that the Ag$_2$WO$_4$.4AgI- and Ce$_{0.95}$Ca$_{0.05}$F$_{2.95}$-based sensors respond to the presence of the listed analytes. Furthermore, the response can be varied by varying the potential of the sensing electrode.

As can be seen from Tables I, II, and III, the sensing electrode potential required to elicit a response to the readily oxidizable compounds, such as CO or CH$_3$N$_2$H$_3$, is only about 0.4 V, whereas a potential of 0.8 V or higher is required to elicit a response to CH$_4$. At the higher potential, these sensors respond not only to methane but also to the more readily oxidizable compounds, such as CO and CH$_3$N$_2$H$_3$. Therefore, to distinguish between methane and the more readily oxidizable compounds, it is necessary to use an array of at least two such sensors, one of which is biased at the methane sensing potential while the other is biased at a potential that is below that required for methane detection (e.g., 0.4-0.6 V).

It has been found from the foregoing that the characteristics of a solid-state ambient-temperature sensor of the present invention include those listed below:

1. The sensor is amperometric in that the current flow upon exposure to a measured analyte tends to be approximately proportional to the analyte concentration.
2. The electrolyte is substantially liquid-free (i.e., free of aqueous or non-aqueous liquids) and water insoluble.
3. The current flow in the electrolyte is ionic rather than electronic.
4. The ionic conductor is chemically stable.
5. Although the sensitivities of these sensors tend to degrade with time, both the Ag$_2$WO$_4$.4AgI- and the Ce$_{0.95}$Ca$_{0.05}$F$_{2.95}$-based sensors have remained responsive to methane after a period of eight months (see Tables I and III).

The preceding examples demonstrate the longevity that can be achieved with solid-state amperometric sensors comprising an electrolyte that is ionically conductive at room temperature and is substantially free of hygroscopic or water-soluble components. Several other solid electrolytes meeting these requirements are listed in Table IV. These and other similar electrolytes should also yield fairly long-lasting ambient-temperature electrochemical sensors.

TABLE IV
ROOM TEMPERATURE CONDUCTIVITIES AND WATER-SOLUBILITIES OF SEVERAL SOLID ELECTROLYTES

| Electrolyte | Ionic Conductivity (ohm-cm)$^{-1}$ | Solubility at 20±5° C. in 100 mL of H$_2$O (g) |
|---|---|---|
| Ce$_{0.95}$Ca$_{0.05}$F$_{2.95}$ | Ca. 0.1 | <0.001 |
| Pb$_{0.78}$Bi$_{0.25}$F$_{2.25}$ | Ca. 10$^{-4}$ | <0.06 |
| Ag$_2$WO$_4$.4AgI | 0.04 | <0.01 |
| Ag$_2$CrO$_4$.4AgI | 0.02 | <0.001 |
| Ag$_2$SeO$_4$.3AgI | 0.06 | <0.03 |
| Ag$_2$HgS$_2$6AgI | 0.15 | Very slightly soluble |
| Ag$_{1.95}$Hg$_{0.40}$Te$_{0.65}$I$_{1.35}$ | 0.09 | Very slightly soluble |
| Ag$_{1.80}$Hg$_{0.45}$Se$_{0.70}$I$_{1.30}$ | 0.10 | Very slightly soluble |
| Ag$_3$HgSe$_2$.AgI | 0.045 | Very slightly soluble |
| Ag$_3$PO$_4$.4AgI | 0.02 | <0.0003 |
| Ag$_4$P$_2$O$_7$.15 AgI | 0.09 | Insoluble |

Although the invention has been described with respect to preferred embodiments, it is not to be so limited as changes and modifications can be made which are within the full intended scope of the invention as defined by the appended claims.

I claim:

1. An amperometric sensor for use in detecting selected analytes comprising two electrodes separated by a solid-state electrolyte and electrical means for operating said sensor in the amperometric mode, said electrolyte being characterized by being substantially water-free, non-hygroscopic, water-insoluble, and having a composition effective to allow an ionic conductivity of at least 10$^{-4}$ ohm$^{-1}$-cm$^{-1}$ at room temperature, wherein said ionic conductivity is predominantly due to a silver ion.

2. A sensor as in claim 1, wherein said electrolyte includes AgI.

3. A sensor as in claim 2, wherein said electrolyte comprises a material selected from the group consisting of Ag$_2$WO$_4$.4AgI, Ag$_2$CrO$_4$.4AgI, Ag$_2$SeO$_4$.3AgI, Ag$_2$HgS$_2$.6AgI, Ag$_{1.85}$Hg$_{0.40}$Te$_{0.66}$I$_{1.35}$, Ag$_{1.80}$Hg$_{0.45}$Se$_{0.70}$I$_{1.30}$, Ag$_3$HgSe$_2$.AgI, Ag$_3$PO$_4$.4AgI, and Ag$_4$P$_2$O$_7$.15AgI.

4. A sensor as in claim 2, comprising a noble metal sensing electrode, a silver counter electrode, and an intermediate layer between said electrolyte and the sensing electrode.

5. The sensor of claim 4, wherein said intermediate layer comprises an oxide.

6. The sensor of claim 5, wherein said oxide comprises silver oxide and said noble metal comprises platinum.

* * * * *